United States Patent
Suharto et al.

(10) Patent No.: US 8,293,246 B2
(45) Date of Patent: Oct. 23, 2012

(54) USES OF RED YEAST RICE IN TREATING DENGUE VIRUS INFECTION

(75) Inventors: Suharto, Surabaya (ID); Erwin Astha Triyono, Sidoarjo (ID)

(73) Assignee: Eu Yan Sang International Limited, Singapore (SG)

( * ) Notice: Subject to any disclaimer, the term of this patent is extended or adjusted under 35 U.S.C. 154(b) by 0 days.

(21) Appl. No.: 13/263,378

(22) PCT Filed: Apr. 7, 2010

(86) PCT No.: PCT/IB2010/051513
§ 371 (c)(1),
(2), (4) Date: Oct. 7, 2011

(87) PCT Pub. No.: WO2010/116336
PCT Pub. Date: Oct. 14, 2010

(65) Prior Publication Data
US 2012/0039996 A1 Feb. 16, 2012

Related U.S. Application Data

(60) Provisional application No. 61/167,640, filed on Apr. 8, 2009.

(51) Int. Cl.
*A61K 36/06* (2006.01)
*A61K 36/899* (2006.01)
*A61K 35/00* (2006.01)
*C12P 21/04* (2006.01)
*C12N 1/00* (2006.01)

(52) U.S. Cl. ........... 424/195.16; 424/750; 424/93.51; 424/780; 435/69.9; 435/255.1

(58) Field of Classification Search .................. None
See application file for complete search history.

(56) References Cited

PUBLICATIONS

Rothwell et al. (2009) Virology 389: pp. 8-19.*
Danuri (2008) Hayati Journal of Biosciences p. 61-66.*
Lee et al. (2008) Journal of Virology vol. 82, No. 13, pp. 6470-6480.*
Medigeshi et al. (2008) Journal of Virology, vol. 82, No. 11, pp. 5212-5219.*

* cited by examiner

*Primary Examiner* — Chris R Tate
*Assistant Examiner* — Russell Fiebig

(57) ABSTRACT

This invention provides a method of using red yeast rice fermented product to treat a subject having a disease caused by dengue virus. In one embodiment, the red yeast rice is prepared with the yeast *Monascus purpureus*.

6 Claims, 1 Drawing Sheet

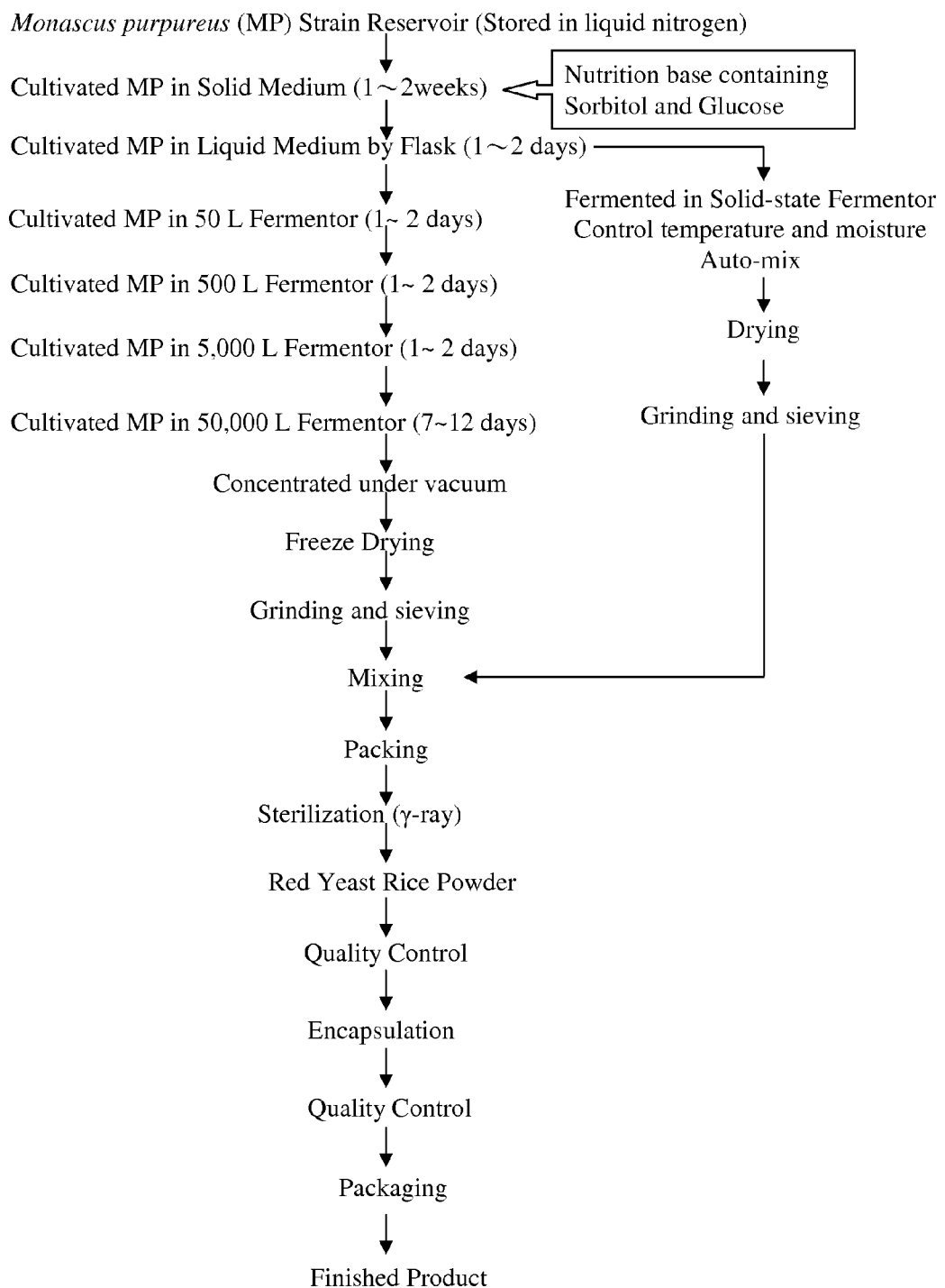

USES OF RED YEAST RICE IN TREATING DENGUE VIRUS INFECTION

CROSS-REFERENCES TO RELATED APPLICATIONS

This application is the National Stage of International Application No. PCT/IB2010/051513, filed Apr. 7, 2010, which claims benefit of U.S. Ser. No. 61/167,640, filed Apr. 8, 2009, the entire contents of which are incorporated by reference into this application.

FIELD OF THE INVENTION

This invention relates to uses of red yeast rice in treating dengue virus infection.

BACKGROUND OF THE INVENTION

Red yeast rice is a traditional food consumed throughout Asia. Its food value and medicinal value is believed to date back more than a thousand years, with the first documentation of its use recorded in 800 A.D. Red yeast rice is sold in jars at Asian markets as pasteurized wet aggregate, whole dried grains, or as ground powder. It was a commonly used red food colouring in East Asian and Chinese cuisine prior to the discovery of chemical food coloring. It has also been used in Chinese herbal medicine.

The yeast *Monascus* isolated from red yeast rice first became known in Western society through the work of Dutch scientists, who noted its use by local populations in Java in 1884. A species isolated from red Koji or Honqu (as red rice yeast is known in East Asia) was named *Monascus Purpureus* Went in 1895, in recognition of the purple coloration. Today there are more than 30 *Monascus* strains on deposit with the American Type Culture Collection.

The traditional method of making red yeast rice is to ferment the yeast naturally on a bed of cooked non-glutinous whole rice kernels. Extracts from red yeast rice contain starch, sterols, isoflavones, and monounsaturated fatty acids, and other compounds. Depending on the *Monascus* strains used and fermentation conditions, it may contain polyketides called monacolins. These monacolins are believed to account for the majority of the cholesterol-lowering activity of the yeast. One of these, "Monacolin K," is a potent inhibitor of HMG-CoA reductase, and is also known as Lovastatin™, a commonly prescribed lipid-lowering drug.

Dengue fever and dengue hemorrhagic fever are caused by one of four closely related, but antigenically distinct, virus serotypes (DEN-1, DEN-2, DEN-3, and DEN-4), of the genus Flavivirus. Infection with one of these serotypes provides immunity to only that serotype for life, so persons living in a dengue-endemic area can have more than one dengue infection during their lifetime. Dengue fever and dengue hemorrhagic fever are primarily diseases of tropical and sub tropical areas, and the four different dengue serotypes are maintained in a cycle that involves humans and the *Aedes mosquito*. However, *Aedes aegypti*, a domestic, day-biting mosquito that prefers to feed on humans, is the most common Aedes species.

In 2005, dengue is the most important mosquito-borne viral disease affecting humans; its global distribution is comparable to that of malaria, and an estimated 2.5 billion people live in areas at risk for epidemic transmission. Each year, tens of millions of cases of dengue fever occur and, depending on the year, up to hundreds of thousands of cases of dengue hemorrhagic fever.

Dengue fever usually starts suddenly with a high fever, rash, severe headache, pain behind the eyes, and muscle and joint pain. The severity of the joint pain has given dengue the name "breakbone fever." Nausea, vomiting, and loss of appetite are common. A rash usually appears 3 to 4 days after the start of the fever. The illness can last up to 10 days, but complete recovery can take as long as a month. Older children and adults are usually sicker than young children.

Most dengue infections result in relatively mild illness, but some can progress to dengue hemorrhagic fever. With dengue hemorrhagic fever, the blood vessels start to leak and cause bleeding from the nose, mouth, and gums. Bruising can be a sign of bleeding inside the body. Without prompt treatment, the blood vessels can collapse, causing shock (dengue shock syndrome). The case-fatality rate of dengue hemorrhagic fever in most countries is about 5%, but this can be reduced to less than 1% with proper treatment. Most fatal cases are among children and young adults.

Because dengue is caused by a virus, there is no specific medicine or antibiotic to treat it. For typical dengue, the treatment is purely concerned with relief of the symptoms (symptomatic). Rest and fluid intake for adequate hydration is important.

No dengue vaccine is available. Recently, however, attenuated candidate vaccine viruses have been developed. Efficacy trials in human volunteers have yet to be initiated. Research is also being conducted to develop second-generation recombinant vaccine viruses. Therefore, an effective dengue vaccine for public use will not be available for 5 to 10 years.

Prospects for reversing the recent trend of increased epidemic activity and geographic expansion of dengue are not promising. New dengue virus strains and serotypes will likely continue to be introduced into many areas where the population densities of *Ae. aegypti* are at high levels. Hence, there is a need for finding new method of preventing and treating diseases caused by the dengue virus.

SUMMARY OF THE INVENTION

Thrombocytopenia is a common complication in patients infected with dengue virus. The present invention presents clinical data that indicate using red yeast rice to treat patients with dengue virus infection results in increased thrombosis. Accordingly, the present invention provides a method of using red yeast rice to treat a subject having a disease caused by dengue virus. In one embodiment, the red yeast rice is a fermented product with the yeast *Monascus purpureus*.

BRIEF DESCRIPTION OF THE DRAWINGS

FIG. 1 shows a flow chart for one embodiment of preparing red yeast rice in capsule form.

DETAILED DESCRIPTION OF THE INVENTION

The following terms shall be used to describe the present invention. In the absence of a specific definition set forth herein, the terms used to describe the present invention shall be given their common meaning as understood by those of ordinary skill in the art.

As used herein, "red yeast rice" is the product of yeast (*Monascus purpureus*) grown on rice, and is served as a dietary staple in some Asian countries. It has also been used for many centuries as food additives and preservative, food colorant, and spice.

The present invention provides a method of using red yeast rice to treat a subject having a disease caused by dengue virus. In general, the dengue virus is one of the four antigenically distinct virus serotypes (DEN-1, DEN-2, DEN-3, and DEN-4). The subject may have a disease of dengue fever or dengue hemorrhagic fever. In one embodiment, treatment with the red yeast rice results in increased thrombosis in the subject.

In one embodiment, the red yeast rice comprises yeast in the genus of *Monascus*. For example, the yeast is *Monascus purpureus*. The *Monascus purpureus* strain is known to contribute high levels of Monacolin K, which is the active component in the product. Other yeast/fungi in the genus of *Monascus* that can contribute high levels of Monacolin K would also be used in the present invention.

The red yeast rice can be formulated into a number of formulations according to standard methods in the art (e.g. Cholestin™, U.S. Pat. No. 6,395,281, etc.). In one embodiment, the red yeast rice is formulated into capsules. For example, the capsule is 400 mg; and the dosage was 3 times×1 capsule. One of ordinary skill in the art would readily devise other formulations of red yeast rice with different dosages and treatment frequency.

The present invention also provides uses of red yeast rice for the treatment of dengue virus infection. In general, the dengue virus infection is dengue fever or dengue hemorrhagic fever. In one embodiment, the red yeast rice comprises yeast in the genus of *Monascus*. In another embodiment, the red yeast rice is formulated into capsules. In yet another embodiment, the treatment comprises taking three red yeast rice capsules per day for seven days.

The invention being generally described, will be more readily understood by reference to the following examples which are included merely for purposes of illustration of certain aspects and embodiments of the present invention, and are not intended to limit the invention.

Example 1

Preparation of Red Yeast Rice Fermented Product

One of ordinary skill in the art would readily prepare red yeast rice in various different formulations. In one embodiment, the red yeast rice was prepared in capsule form. Temperature, moisture, oxygen content (%) and fermentation period are critical conditions for the fermentation process. One of ordinary skill in the art would readily adjust the conditions of fermentation to obtain desirable results. In one embodiment of the fermentation process, a nutrition base containing sorbitol and glucose was used. A flow chart for the preparation of red yeast rice in capsule form is shown in FIG. 1.

In one embodiment, specifications of *Monascus purpureus* powder include:
Appearance: Brick red powder
Loss on Drying: <8.0%
Total Plate Count: <1×10$^3$ cfu/gm
*E. coli*: Negative
Yeast & Mold: <1×10$^2$ cfu/gm
Heavy Metals: <10.0 ppm
As: <2.0 ppm
Monacolin K (by HPLC): >2.2 mg/gm
Citrinin* (by HPLC): N.D.
*Limit of detection=0.010 ppm In one embodiment, the shelf life of red yeast rice powder is about 2 years.

Example 2

Preliminary Clinical Studies

Dengue virus infection is a self-limiting disease with a recovery period of approximately 7 days. But in the process of disease resolution, complications often occur. One complication is plasma leakage or fluid accumulation in the body's cavity, a condition that may lead to shock, i.e. failure of blood circulation system to circulate blood to the body's vital organs. Another complication is hemorrhage which is mainly caused by disturbed/effected thrombosis (thrombocytopenia or thrombopathy).

Currently, there is no scientifically proven method that can increase the number/level of thrombosis in dengue infected patients. Clinical staff thus usually takes on a more passive approach and will only react when the thrombocytopenia causes bleeding or is life threatening. The present example presents experiments that are designed to monitor and understand changes of thrombosis number/levels in dengue virus-infected patients who have received *Monascus purpureus* (red yeast rice) therapy.

Selected patients (with dengue infection) were clinically proven and suit the research criteria. Thrombosis was monitored in a serial manner every 24 hours. The patients were monitored for a period of 7 days (during the course of their sickness). Red yeast rice (*Monascus purpureus*) was administered to the patients with a dosage of 3×1 capsule for a period of 7 days during the course of their sickness. Administered capsules were 400 mg each. Dosage was 3 times×1 capsule.

Patients' characteristics were shown in Table 1. Increased thrombosis after treatment with red yeast rice was shown in Table 2. Eleven patients (64.7%) displayed immediate response in increased thrombosis after receiving therapy. The mean of response in increased thrombosis after receiving therapy was 1.7 days. No side effect was found. Further analytical research is required using a larger sample as well as using multicentre research trial.

TABLE 1

| Subject Characteristics (n = 19) | | |
|---|---|---|
| | n | % |
| Sex | | |
| Man | 15 | 79 |
| Woman | 4 | 21 |
| Age | | |
| 14-25 | 13 | 68.4 |
| 26-50 | 6 | 31.6 |
| Length of period of fever before being admitted to hospital | | |
| 1 day | 2 | 10.6 |
| 2 days | 3 | 15.8 |
| 3 days | 6 | 31.6 |
| 4 days | 5 | 26.3 |
| 5 days | 3 | 15.8 |
| 6 days | 0 | 0 |
| Mean (days) | 3.2 | |
| Diagnostic Criteria | | |
| IgM Antidengue | 1 | 5 |
| IgG Antidengue | 4 | 20 |
| IgM & Ig G Antidengue | 7 | 35 |
| NS 1 | 8 | 40 |
| Diagnosis | | |
| Dengue Fever | 0 | 0 |
| Dengue Haemorrhagic Fever 1 | 16 | 84.2 |
| Dengue Haemorrhagic Fever 2 | 3 | 15.8 |

TABLE 2

| Therapy Results | | |
|---|---|---|
| | n | % |
| Response to increased Thrombosis | | |
| 1 day after therapy | 11 | 64.7 |
| 2 days after therapy | 3 | 17.6 |

TABLE 2-continued

Therapy Results

|  | n | % |
|---|---|---|
| 3 days after therapy | 0 | 0 |
| 4 days after therapy | 3 | 17.6 |
| Mean (days) | 1.7 | |

Example 3

Double Blind Multi-Center Trials

This clinical research will use the double blind randomized controlled trial method, involving patients who are infected with the dengue virus and have been clinically proven to have met the WHO 1997 diagnosis criteria. One of ordinary skill in the art would readily design clinical trials in various formats, and what is described below is one example of clinical trial.

Patients in the treatment group will be given *Monascus purpureus* (red yeast rice) with a dosage of 3×1 capsules while those in the control group are given placebo. These patients will be tracked for 7 days (during the fever period). During this period, the following parameters will be monitored: a complete blood test (especially the thrombocyte thrombosis or blood platelet; in a series of every 24 hours), and physical examination and clinical signs.

Patient inclusion criteria include: patient must be
1. Male or female aged 14 until 65 years.
2. Has had fever for <3 days.
3. Positive for rumpel-ledee test or showing signs of light, spontaneous hemorrhage (petechiae, ecchymosis).
4. Positive for NS-1 dengue virus test
5. Agrees to remain hospitalized till study completion and agreeable to be part of the research by signing the patient informed consent form.

Patient exclusion criteria include
1. Has received overnight hospital care for 2 days.
2. Has undergone whole blood transfusion, PRC, platelet, FFP during period of care.
3. Experienced serious complications: DIC, shock, medium/serious hemorrhage (DHF 3rd/4th degree), decrease in level of consciousness (encephalopathy).
4. Has other serious conditions like abnormal haematology (ITP, leukemia, hemophilia and others), heart disease (hereditary heart disease, RHD, myocarditis, heart failure) and lung disease (bronchial asthma and others).
5. Is on HMG-CoA reductase inhibitors, such as atorvastatin and lovastatin.
6. Is on high-dose nicotinic acid (more than 1,000 mg/per day).
7. Has allergy or has experienced other serious side effects.
8. Is a transplant recipient.
9. Female who is breast-feeding or pregnant.

In one embodiment, total minimum sample size can be calculated based on the formulae below:

$$n = \frac{2(Z\alpha + Z\beta)^2 \cdot \sigma^2}{(\mu 1 - \mu 2)^2}$$

wherein n is the sample size per group;

α is the mean level as set by researcher (here it is set as 0.05);

Zα is adjusted standard deviation, the final sum depends on α. If α=0.05, then the value will be 1.96;

β is the power of test. Here it is set as 0.20; so Zβ=0.84;

μ1 is average increase in thrombosis among patients in treatment group;

μ2 is average increase in thrombosis among patients in control group;

σ=σ1 is the SD increase in thrombosis among patients in treatment group;

σ2 is the SD increase in thrombosis among patients in control group.

Based on previous researches, numbers obtained have shown that μ1=100.3; μ2=40.3 and σ=50.5, so n for each group=12; with anticipated dropout rate of 10% to become 15. Thus the total sample size=2×15=30 patients/sample area group. Should there be 4 area groups, there will be a need to obtain a sample size of 30×4=120.

The following statistical analysis will be used:
Independent Qualitative Test 2-sample: Chi-square
ANOVA Test (analysis of variance), used to compare the thrombosis performance between the treatment group and the control group. In one embodiment, it can also be used to compare changes in GM-CSF and IL-3 contents between the treatment group and the control group.

Independent T-Test 2-sample used to compare the thrombosis performance between treatment group and control group among different strata. In one embodiment, it can also be used to compare the changes in GM-CSF and IL-3 contents between the treatment group and control group.

Independent T-Test 2-sample is used to compare between respective strata, the thrombosis performance on the treatment group and the control group. In one embodiment, it can also be used to compare changes in GM-CSF and IL-3 contents in the treatment group and the control group.

Multivariate Analysis

TIME AND EVENT SCHEDULE

| | Assessment No | | | | | | |
|---|---|---|---|---|---|---|---|
| | 1 | 2 | 3 | 4 | 5 | 6 | 7 |
| | Day | | | | | | |
| | Day 1 | Day 2 | Day 3 | Day 4 | Day 5 | Day 6 | Day 7 |
| Informed consent | • | | | | | | |
| Randomization | • | | | | | | |
| Medical History | • | | | | | | |
| Physical Exam | • | • | • | • | • | • | • |
| Clinical Signs/ Symptom response | • | • | • | • | • | • | • |
| NS-1 | • | | | | | | |
| Haematology (CBC) | • | • | • | • | • | • | • |
| Compliance Check | | • | • | • | • | • | • |
| Drug Administration | • | • | • | • | • | • | • |
| Adverse event | | • | • | • | • | • | • |

What is claimed is:

1. A method for treating a subject having an illness caused by infection with a dengue virus, comprising administering an effective amount of red yeast rice to the subject, wherein the yeast in the red yeast rice is *Monascus purpureus*.

2. The method of claim 1, wherein the dengue virus is of serotype DEN-1, DEN-2, DEN-3, or DEN-4.

3. The method of claim 1, wherein the illness is dengue fever or dengue hemorrhagic fever.

4. The method of claim 1, wherein treatment with the red yeast rice results in increased thrombosis in the subject.

5. The method of claim 1, wherein the red yeast rice is formulated into capsule form.

6. The method of claim 5, wherein the treatment comprises administering three of the red yeast rice capsules per day for seven days.

* * * * *